United States Patent [19]

Polaschegg

[11] Patent Number: 4,796,644

[45] Date of Patent: Jan. 10, 1989

[54] APPARATUS FOR INFUSION AND REMOVAL OF SAMPLES OF BLOOD AND OTHER BODY FLUIDS

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 884,128

[22] Filed: Jul. 10, 1986

[30] Foreign Application Priority Data

Jul. 11, 1985 [DE] Fed. Rep. of Germany ....... 3524824

[51] Int. Cl.⁴ .............................................. A61B 5/00
[52] U.S. Cl. .................... 128/760; 128/765; 128/766; 604/4; 604/151
[58] Field of Search .............. 128/760, 762, 765, 766, 128/763, DIG. 3; 604/4, 29, 151, 152, 153

[56] References Cited

U.S. PATENT DOCUMENTS

| | | | |
|---|---|---|---|
| 3,946,731 | 3/1976 | Lichtenstein | 604/66 |
| 4,077,395 | 3/1978 | Woolner | 128/DIG. 5 |
| 4,258,717 | 3/1981 | Bisera et al. | 128/637 |
| 4,479,761 | 10/1984 | Bilstad et al. | 604/153 |
| 4,552,552 | 11/1985 | Polaschegg et al. | 604/4 |

FOREIGN PATENT DOCUMENTS

WO84/04033  5/1984  World Int. Prop. O.

*Primary Examiner*—Edward M. Coven
*Assistant Examiner*—Randy Citrin
*Attorney, Agent, or Firm*—Townsend and Townsend

[57] ABSTRACT

Apparatus for infusion and removal of samples of blood and other body fluids comprising a blood connection which is connected via a first line to a sample taking means, a pump connected to the first line, a container connected to the first line via a second line and containing an aqueous fluid, a first shut-off means connected into the second line and a control means for activating the first shut-off means and the pump, the control means switching the shut-off means and the blood pump alternately into fluid supply mode and blood removal mode.

10 Claims, 1 Drawing Sheet

APPARATUS FOR INFUSION AND REMOVAL OF SAMPLES OF BLOOD AND OTHER BODY FLUIDS

BACKGROUND OF THE INVENTION

In intensive medicine the determination of blood values, for example of the total protein or the electrolyte, is of particular signigicance. If for example during an intensive treatment an infusion therapy by means of potassium is carried out a practically continuous monitoring of the blood potassium values is necassary because an ovedose or inadequate dose can have serious consequences.

In such a therapy for monitoring the blood values usually the blood necessary for the investigation is take from the patient via a separate additional blood connection, for example a catheter. A disadvantage is then however that the patient is additionally subjected to the strain of this further blood removal catheter.

German Pat. No. 3,313,074 discloses an apparatus with which blood and other body fluids can be taken from a patient and supplied to a sample taking device. After withdrawal of coagulable body fluids the device is intermittently flushed with a flushing solution, whereupon the withdrawal operation starts again. The known apparatus is however not used for infusion of a fluid and is rather a block sampling means which is used in addition to an infusion apparatus and this leads to the disadvantages mentioned above.

German specification as laid open to inspection No. 2,644,062 and German Pat. No. 3,235,744 disclose single-needle hemodialysis apparatuses in which blood is led in an extracorporeal cycle through a dialyzer and freed there from metabolism products. Such a hemodialysis machine is however neither an infusion apparatus nor a sample taking apparatus but rather a blood cleaning machine which serves for purification and not for infusion or taking samples.

SUMMARY OF THE INVENTION

The invention is therefore based on the problem of further developing the apparatus for infusion and removal of samples of blood in such a manner that an infusion can also be carried out.

This problem is solved according to a first embodiment in that the one end of the first line is returned to form a closed cycle to the other end of the first line, the sample taking means being connected into the first line and dividing the first line into an incoming line and an outgoing line, the filling volume of the pump is considerably greater than the filling volume of the blood connection up to the connection point with the first line and the container comprises an infusion solution, and in according with a second embodiment that the pump is connected to the other end of the first line and has a filling volume which is substantially greater than the internal volume of the first line, the sample taking means is connected into the first line, the first line has in the region of the blood connection a second shut-off means and the container comprises an infusion solution.

According to the invention an apparatus is now made available with which via a single blood connection both an infusion and a removal of blood or other body fluids can be carried out. This reduces the in any case great strain on the patient to a minimum, simultaneously ensuring monitoring of the blood taken from the patient during the infusion.

During the therapy the apparatus according to the invention can be switched by the control means alternately in accordance with a predetermined program, i.e. at predetermined intervals, from the infusion mode to the blood taking mode and vice versa. According to the invention the shut-off means arranged in the line system can be switched at intervals of time from infusion operation to blood taking operation and vice versa. The shut-off means disposed in the line system are actuated differently in the manner of a pump preferably constructed as reciprocating piston pump and switched alternately into expansion mode (filling mode) and compression mode (evacuating mode). This pump is subjected equally in succession both to the infusion solution and to blood or other body fluids, it being ensured that all the fluids are conveyed back to the patient, i.e. all the fluids pass through the extracorporeal system only for a short period of time. There is thus no danger of the extracorporeal line system becoming clogged by coagulation of blood or other body fluids. This is moreover preferably prevented in that the infusion solution simultaneously serves as flushing solution so that in the infusion operation of the apparatus according to the invention following the blood taking operation the blood disposed in the extracorporeal cycle is displaced by the infusion solution, at the same time a free flushing of the entire extracorporeal system taking place.

According to a first preferred embodiment the extracorporeal cycle is conducted in a closed cycle which has only one connection leading to the patient. Furthermore, this cycle is connected to at least one infusion solution container and in addition into the cycle a sample taking means is connected at which either blood samples can be taken or alternatively the blood parameters can be measured.

Suitable as such sample taking means are for example throughflow sensors with which certain blood parameters, for example the sodium, potassium or calcium content of the blood, the hematocrit value, the conductivity of the blood, and the like can be measured.

On the other hand, however, alternatively a membrane filter may be used as sample taking means at which for example blood plasma can be removed, in which the aforementioned parameters can be determined in a further device. Additionally, further parameters, for example protein fractions and the like, the plasma comprising such proteins, can be determined.

Finally, as blood taking means it is of course possible to provide a blood taking point at which for example by means of a syringe blood is removed which is analyzed in a further analyzer.

According to this first embodiment it is thus possible to cycle both the infusion solution and the blood, and a recirculating region is to be found only in the region of the connection of the extracorporeal system to the catheter.

According to a preferred second embodiment the one side of an extracorporeal flexible tube system is connected to the catheter whilst the other side of the tube is connected to the pump chamber. Connected into said tube is the sample taking means so that on aspiration via the pump blood is constrained to pass through the blood taking station. After filling the pump the blood is pumped back along the same path to the patient. Thereafter the entire extracorporeal system is again filled with infusion solution, a cleaning of the system simultaneously taking place.

According to the invention it is important that the fluids disposed in the extracorporeal tubing system do not disturb or falsify the sample taking operation, in particular the direct measurement of the blood parameters. In this respect it must therefore be ensured that the pump in the blood taking mode takes up all infusion solution residues remaining in the extracorporeal tubing system and in addition the blood constituents mixed with said residues so that in the sample taking means after the complete filling of the pump a blood sample free from contaminations can pass to the measurement.

Advantageously, the absorption capacity of the pump corresponds at least substantially to the filling volume of the extracorporeal system which extends from the tip of the catheter up to the blood pump. This ensures that all the infusion fluid residues remaining in the extracorporeal system can be taken up by the pump and in addition a certain blood residue contaminated with infusion solution is partially taken up by the pump and partially remains in the line remainder which leads downstream of the sample taking means to the pump according to the second embodiment.

The subsidiary claims relate to advantageous further developments of the invention.

BRIEF DESCRIPTION OF THE DRAWINGS

Further details, features and advantages of the invention will be apparent from the following description of two examples of embodiment with the aid of the drawings, wherein.

DETAILED DESCRIPTION OF THE PREFERRED EMBODIMENTS

Figure 1:
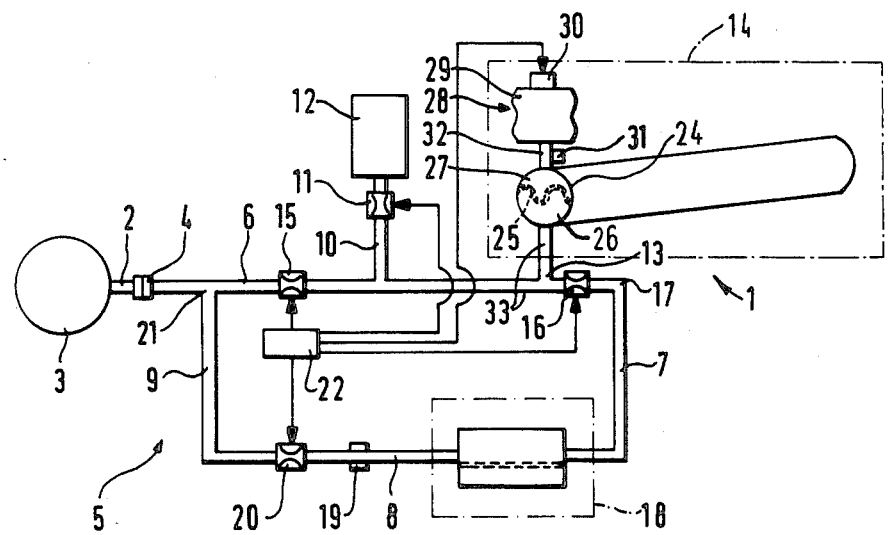
FIG. 1 is a schematic illustration of a first embodiment of the apparatus according to the invention and FIG. 2 is an illustration of a second embodiment of the apparatus according to the invention corresponding to FIG. 1.

A first embodiment of the apparatus 1 according to the invention shown in FIG. 1 for taking samples and infusion comprises a blood connection 2 which can be made in the form of a conventional catheter. The blood connection 2 is inserted into the patient represented in FIG. 1 by means of the circle 3. Connected to the blood connection 2 via a connector 4 is a line system which in the example of embodiment consists of four line sections 6, 7, 8 and 9. Connected to the line section 6 is a first branch line 10 in which a shut-off means 11 is disposed and which communicates with an infusion solution container 12. Further connected to the first line section 6 is a second branch line 13 which communicates with a pump 14 which is preferably constructed as pneumatically driven pump.

Furthermore, in the line section 6 between the blood connection 2 and the branch line 10 a shut-off means 15 is disposed. A further shut-off means 16 is disposed in the line section 6 between the pump 14 and a branch point 17 in the line section 6 and the line section 7.

Provided in the line section 8 is a measuring means 18 by means of which the blood parameters to be investigated can be determined. Furthermore, the line section 8 has an air detector 19 and a further shut-off means 20 which is disposed between the measuring means 18 and the return point 21 of the line section 9 in the line section 6.

Furthermore, a schematically simplified control means 22 is provided serving to control the shut-off means 11, 15, 16 and 20. Below, the principle of the mode of operation of the apparatus 1 according to the invention will be described.

By the preferably pneumatically driven pump 14 by suitable switching of the shut-off means 11, 15, 16 and 20 as desired either blood can be taken from the patient or infused back via the measuring and/or sample taking means 18 (hereinafter sample taking means 18) or infusion solution from the infusion solution container 12 infused into the patient. For this purpose for taking samples the shut-off means 11, 16 and 20 are closed whilst the shut-off means 15 is open. In this state the pneumatic pump 14 can extract blood from the patient. Once the suction operation is terminated the shut-off means 15 is closed and the shutoff means 16 and 20 are opened. The pump 14 then compresses and conveys the extracted blood via the sample taking means 18 back into the patient. Once the sample taking and measurement are concluded the apparatus 1 according to the invention can be switched over to infusion.

For this purpose the shut-off means 15 is first closed whilst for drawing off infusion solution the shut-off means 11 is opened. Thereafter for the infusion the shut-off means 11 is closed again whereas the shut-off means 16 and 20 are opened. In this state of the shut-off means the infusion solution drawn off by the pump 14 is supplied to the patient via the line sections 7, 8, 9 and the portion of the line section 6 leading from the connector 4 to the return point 21.

As an alternative to this switching of the shut-off means described above it is however also possible after the drawing off of the infusion solution to close the shut-off means 16 and open and shut-off means 15, whereafter the infusion solution can be conveyed directly to the patient via the line section 6.

The following marginal conditions are to be observed for the function of the apparatus 1:

The region of the line section 6 between the point 21 and the shut-off means 15 which is not continuously flushed through should be kept as short as possible to stop blood becoming stationary therein and coagulating. The pump volume of the pneumatic pump 14 should be made large enough the ensure that the blood or fluid is not moved simply to and fro but in fact taken from the patient and returned again. This means that the pump volume of the pump 14 must be appreciably greater than the filling volume of the catheter up to the point 21. In this respect the previously described second possibility for infusion only via the line section 6 has the advantage that in this manner blood disposed in this region of the apparatus can be returned to the patient by means of the infusion solution. If the two previously described infusion possibilities are carried out in succession it is possible in this manner to free the entire apparatus from blood residues.

Figure 2:
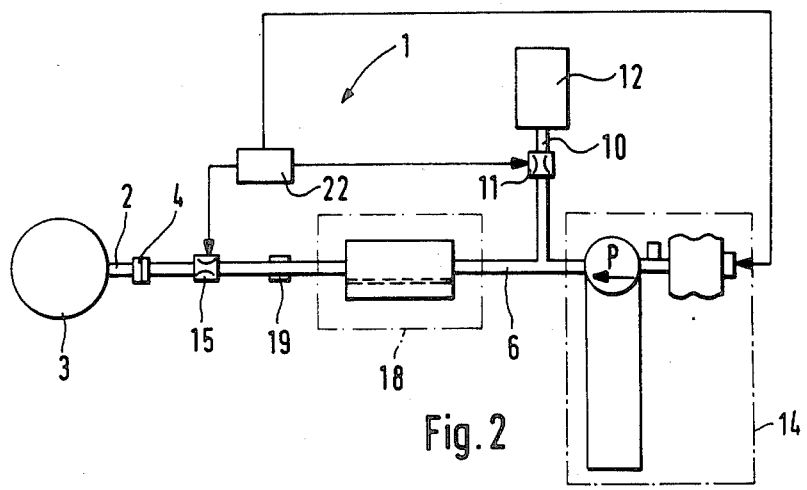

FIG. 2 shows a constructionally simplified embodiment of the apparatus 1 according to the invention. In the following description identical parts are provided with the same reference numerals as in FIG. 1.

As apparent from the illustration the embodiment of the apparatus 1 illustrated in FIG. 2 has only two shut-off means 15 and 11 which are disposed in the line section 6 or in the in this case only branch line 10. As regards its function the second embodiment differs from the first in that in the sample taking mode the blood is not circulated but merely pumped forwards and backwards.

For taking a sample the pump 14 is first compressed, the valve or shut-off means 11 closed and the valve or shut-off means 15 opened. Blood can then be withdrawn, initially infusion solution being sucked back from the blood connection 2 and blood then following. At the upper dead centre of the pump 14 a sample can then be taken, whereafter the blood is infused back. Thereupon the pump 14 is operated as infusion pump, in the withdrawal operation the shut-off means 15 being closed whilst the shut-off means 11 is open. On conveying infusion solution, however, the shut-off means 11 is closed and the shut-off means 15 open. As regards the functionability of this embodiment it must be assumed that the pump volume of the pump 14 is substantially greater than the volume of the line from the pump 14 up to the end of the blood connection 2.

As apparent from FIGS. 1 and 2 the pump serves to convey the infusion solution or the blood or body fluids. Advantageously, said pump 14 is constructed as pneumatic pump and as shown in FIGS. 1 and 2 comprises a pump chamber (24) which is divided by a flexible membrane or diaphragm (25) into a first pump chamber section (26) and a second pump chamber section (27).

The two first and second pump chamber regions form together the internal volume $V_1$ of the pump chamber (24).

The flexible membrane (25) can move in opposite directions, depending on the operating phase of the pump, the compression or expansion phase, until it bears completely on the inner wall of the pump chamber. This is for example shown in the embodiment of FIG. 2 in the expansion state of the pump 14.

As apparent from the drawings the pump chamber (24), in particular the second pump chamber portion (27) is connected via a connecting line (32) to the drive member (28) consisting of a pneumatically operated bellows (29), a drive motor (30) and a valve unit (31).

The first pump chamber portion (26) is however connected to the line section (6) via a further connecting line (33). It should be mentioned that this intermediate line (33) can also be omitted, i.e. the first pump chamber portion (26) can be connected directly into the line (6).

The bellows (29) can either be compressed or expanded by the drive motor (30), the switching of the pump (14) from the one to the other phase taking place at the lower and upper dead centres of the pump. Synchronously with this switchover the switching over of the shut-off members (11, 15, 16 and 20) to the other operating phase by the control unit (22) takes place.

Finally, it is pointed out that the valve unit (31) can be used for venting the connecting line (32) and thus the bellows (29) in accordance with a predetermined program as for example described In DE-OS No. 3,205,449 corresponding to U.S. Pat. No. 4,552,552, incorporated herein be reference, which also describes such a bellows pump.

As already mentioned the internal volume $V_1$ of the pump chamber (24) is substantially greater than the internal volumes of the lines including the catheter so as to prevent a pumping to and fro of the infusion solution or the blood in the line system. Preferably, the volume of the pump chamber is at least twice as great as the total internal volume of the line system.

As already mentioned as sample taking unit (18) an electrochemical sensor system may be used with which advantageously selectively specific blood parameters, for example sodium, potassium or calcium ions, may be detected. Such an arrangement is described for example in DE-OS corresponding to U.S. patent application Ser. No. 06/732,022 to the disclosure of which express reference is made.

Of advantage when using electrochemical sensors is the fact that the solution to be infused because of its constant composition can be used as flushing solution and calibration standard for the electrochemical sensor between respective determinations of the blood parameters so that every time the exactly calibrated measuring arrangement is available for the measurement to be carried out.

It is additionally pointed out that the apparatus described need not necessarily be simultaneously used as infusion pump. However, to avoid coagulation of the blood it is advantageous after the measurement to at least flush free the sample taking and measuring means with an infusion solution. If part of this solution is also infused into the patient this part must be included in the calculation of the fluid and substance balance.

I claim:

1. Apparatus for taking samples of body fluids from a living body, said apparatus comprising:
   a single needle means to connect with a living body for withdrawing body fluids from the living body;
   a first valve (15);
   a second valve (11);
   conduit means coupled at least to said first valve, to said second valve and to said needle means for carrying fluid between said first valve, said second valve and said needle means;
   a reciprocating pump (14);
   control means coupled at least to said first valve and to said second valve for alternately switching said first valve and said second valve open and closed to control said reciprocating pump in an infusion mode and a removal mode;
   an infusion fluid supply (12) coupled to said second valve; and
   means (18) for extracting samples of the body fluid from said conduit means;
   said second valve disposed between said infusion fluid supply and said pump for controlling fluid access between said infusion fluid supply and said pump;
   said first valve being disposed between said pump and said needle means for controlling body fluid access between said pump and the body;
   said samples extracting means being disposed between said pump and said needle means for taking samples at least of body fluids from the body;
   the filling volume of said pump (14) being substantially greater than the filling volume of the the conduit means.

2. The apparatus of claim 1, wherein said control means (22), in the infusion mode, comprises means for switching said pump (14) to an expansion phase, means for opening said first valve (11) and means for closing said second valve (15), and wherein said control means (22), after having filled said pump (14), comprises means for switching said pump (14) to a compression phase, means for closing said first valve (11) and means for opening said second valve (15).

3. The apparatus of claim 2, wherein said control means (22) in the blood removal mode, comprises means for closing said first valve (11) means for opening said second valve (15) and means for switching said pump (14) to the expansion phase thereby supplying blood taken from the patient through said means for extracting samples (18), and wherein said control means (22) thereafter comprises means for switching said pump (14) to the compression phase and, after having emptied said pump (14), switching said pump (14) to the infusion mode.

4. The apparatus according to claim 1, wherein said pump (14) is a pneumatically operated pump which is operated in a compression phase and an expansion phase.

5. The apparatus according to claim 1 wherein an air detector (19) is provided in said first line (6, 7, 8, 9).

6. Apparatus for infusion and removal of samples of blood and other body fluids comprising:
   connecting means (2) for connecting to a living body for extracting body fluids from the living body;
   a first line connected to said connecting means (2);
   means (18) for extracting samples of the body fluid from said first line;
   a reciprocating pump (14);
   said first line including two ends being connected to each other to form a closed loop;
   said first line comprising first and second incoming line segments (6, 7) connected in series and first and second outgoing line segments (8, 9) connected in series, said second incoming line segment connecting at a first end of said samples extraction means and said first outgoing line segment being connected at a second end of said samples extraction means;
   a container (12) for containing an infusion solution and being connected to said first line via a second line (10);
   first shut-off means (11) being disposed in said second line (10) for controlling flow through said second line;
   second shut-off means (15) being disposed between a first point (21) connecting said first incoming line segment (6) and said second outgoing line segment (9) and a second point connecting said first incoming line segment (6) and said second line (10);
   third shut-off means (16) being disposed in said first incoming line segment (6) downstream of said pump (14) for controlling flow through said first incoming line segment;
   fourth shut-off means (20 disposed in said first outgoing line segment (8) for controlling flow through said first outgoing line segment;
   a control means (22) for cooperatively controlling operation of at least said first shut-off means, said second shut-off means, said third shut-off means and said fourth shut-off means;
   said pump being connected to said first incoming line segment (6) downstream of said second shut-off means (15);
   the filling volume of said pump (14) being substantially greater than the filling volume of said first line; and said control means (22) for alternately switching said first and second shut-off means and said pump in an infusion mode and a removal mode, respectively.

7. The apparatus of claim 6 wherein said control means (22) in said infusion mode comprises means for switching said pump (14) to an expansion phase, means for opening said first shut-off means (11) and means for closing said second and third shut-off means (15, 16), and wherein said control means (22), during an evacuating stroke, comprises means for switching said pump (14) to a compression phase, means for closing said first shut-off means (11) and means for opening one of either said second shut-off means (15) or said third and fourth shut-off means (16, 20).

8. The apparatus of claim 7, wherein said control means (22), in the blood removal mode, comprises means for closing said first shut-off means (11), means for opening said second shut-off means (15), means for closing said third and fourth shut-off means (16, 20) and means for switching said pump (14) to an expansion phase and wherein said control means (22), after having filled said pump (14), comprises means for switching over said shut-off means (15, 16, 20) and said pump (14) to a comprssion phase.

9. The apparatus according to claim 6, wherein an air detector (19) is provided in said first line (6, 7, 8, 9).

10. The apparatus according to one of claims 6, wherein said pump (14) is a pneumatically operated pump which is operated in a compression phase and an expansion phase.

* * * * *